US008968799B2

(12) United States Patent
Beggan

(10) Patent No.: US 8,968,799 B2
(45) Date of Patent: Mar. 3, 2015

(54) TIME DELAYED RELEASE MECHANISM FOR ENERGIZING COMPOSITION AND METHOD OF USE

(75) Inventor: Cathy Beggan, Sparta, NJ (US)

(73) Assignee: Rise-N-Shine L.L.C., Sparta, NJ (US)

( * ) Notice: Subject to any disclaimer, the term of this patent is extended or adjusted under 35 U.S.C. 154(b) by 557 days.

(21) Appl. No.: 12/587,173

(22) Filed: Oct. 2, 2009

(65) Prior Publication Data
US 2010/0151023 A1 Jun. 17, 2010

Related U.S. Application Data

(63) Continuation-in-part of application No. 12/220,721, filed on Jul. 28, 2008, now abandoned, which is a continuation of application No. 11/514,500, filed on Sep. 1, 2006, now abandoned.

(51) Int. Cl.
| | | |
|---|---|---|
| A61K 36/25 | (2006.01) | |
| A61K 36/00 | (2006.01) | |
| A61K 31/525 | (2006.01) | |
| A61K 31/4415 | (2006.01) | |
| A61K 31/51 | (2006.01) | |
| A61K 31/714 | (2006.01) | |
| A61K 36/254 | (2006.01) | |
| A61K 36/258 | (2006.01) | |
| A61K 36/77 | (2006.01) | |

(52) U.S. Cl.
CPC ........... *A61K 31/525* (2013.01); *A61K 31/4415* (2013.01); *A61K 31/51* (2013.01); *A61K 31/714* (2013.01); *A61K 36/254* (2013.01); *A61K 36/258* (2013.01); *A61K 36/77* (2013.01)
USPC .......................................... 424/728; 424/725

(58) Field of Classification Search
None
See application file for complete search history.

(56) References Cited

U.S. PATENT DOCUMENTS

| 5,925,377 | A  | * | 7/1999  | Gerth et al. ................... | 424/451 |
|---|---|---|---|---|---|
| 6,139,875 | A  | * | 10/2000 | Adams et al. ................. | 424/476 |
| 6,193,973 | B1 | * | 2/2001  | Tuttle ............................ | 424/728 |
| 6,534,085 | B1 | * | 3/2003  | Zeligs .......................... | 424/451 |
| 6,562,869 | B1 | * | 5/2003  | Hamilton et al. ............. | 514/557 |
| 2002/0136782 | A1 | * | 9/2002  | Fleischner ................... | 424/725 |
| 2003/0012824 | A1 | * | 1/2003  | Ott et al. ...................... | 424/602 |
| 2004/0230257 | A1 | * | 11/2004 | Ovokaitys ..................... | 607/88 |
| 2005/0220878 | A1 | * | 10/2005 | Fegely et al. ................. | 424/473 |
| 2005/0249827 | A1 | * | 11/2005 | Gardiner et al. .............. | 424/729 |
| 2005/0272690 | A1 | * | 12/2005 | Cremisi ......................... | 514/52 |
| 2006/0112584 | A1 | * | 6/2006  | Jones ............................. | 34/60 |
| 2006/0246129 | A1 | * | 11/2006 | Linardakis et al. .......... | 424/451 |
| 2007/0031568 | A1 | * | 2/2007  | Gardiner et al. .............. | 426/597 |

FOREIGN PATENT DOCUMENTS

| WO | WO 88/01865 A1 | * | 3/1988 |
|---|---|---|---|
| WO | WO 94/01006 A2 | * | 1/1994 |

OTHER PUBLICATIONS

Vitamin B complex from Wikipedia online, pp. 1-5, accessed on Mar. 29, 2009.*

* cited by examiner

*Primary Examiner* — Qiuwen Mi
(74) *Attorney, Agent, or Firm* — Ward & Zinna, LLC

(57) ABSTRACT

The present invention is directed to a time-release energizing supplement of the present invention comprising energizing ingredients coated by an enteric coating. The energizing ingredients comprise guarana seed extract, eleuthero root extract, tyrosine, and high amounts of B-complex vitamins. The B-complex vitamins preferably comprise thiamin, riboflavin, niacin, vitamin B6, and vitamin B12. The enteric coating of the time-release energizing supplement controls the release of the energizing ingredients inside the user's body and energizes the user by enhancing physical and metal performance over an extended period of time.

20 Claims, 3 Drawing Sheets

TIME DELAYED RELEASE MECHANISM FOR ENERGIZING COMPOSITION AND METHOD OF USE

This application is a continuation-in-part of U.S. application Ser. No. 12/220,721, filed Jul. 28, 2008 now abandoned, which is a continuation of U.S. application Ser. No. 11/514,500, filed Sep. 1, 2006, now abandoned.

FIELD OF INVENTION

The present invention is generally directed to controlled release of energizing ingredients in tablet or capsule form. In particular, the present invention is directed to delayed and sustained release of energizing ingredients that are designed to energize the user by enhancing physical and metal performance over an extended period of time.

BACKGROUND OF THE INVENTION

Presently, lack of sleep has become a common problem for many people. Consequently, people with insufficient sleep struggle to wake up on time in the morning, even with the aid of an alarm clock. Sleep deprivation could also cause daytime sleepiness and grogginess. Although stimulants such as caffeine, nicotine, and/or ephedrine in the form of coffee, cigarettes and/or energy drinks are widely consumed as means to increase alertness and energy in the morning, such method does not always help one to wake up on time, as one must first awaken in order to ingest these stimulants. Moreover, even after a cup of coffee or a typical energy supplement causes the sudden burst of energy and alertness in the user, the effect wears off quickly after a few hours. This sudden drop of energy, known as an "energy crash", is often linked to diminished productivity and injuries resulting from accidents. Thus, the user often requires additional dosages of stimulants, sometimes leading to over-consumption thereof.

In addition to the above problems associated with common stimulants, many such "energy-producing" stimulants can be addictive and even harmful to the body. For example, ephedrine, a sympathomimetic amine that resembles amphetamine in its structure, can produce adverse reactions, such as hypertension, palpitations, neuropathy, myopathy, psychosis, stroke, memory loss, heart rate irregularities, insomnia, nervousness, tremors, seizures, and heart attacks.

Coffee, despite many health benefits it could bring, cannot be tolerated by those with a sensitive stomach. Moreover, an exaggerate consumption of coffee may cause an addiction. Overconsumption of caffeine can cause nervousness, tremulous hands and fast heart rhythm.

Nicotine, another popular stimulant, is often consumed by means of cigarettes. Aside from the common knowledge that cigarette smoking is a high risk factor for cancer, health consequences of cigarette smoking also include cardiovascular and respiratory diseases. Moreover, nicotine has a powerful addictive property which causes unpleasant withdrawal symptoms.

There is therefore a need for a means to energize the user safely and effectively without the undesired side effects. Furthermore, there is also a need for an energizing supplement that helps the user to wake up on time with minimal inconvenience. The energizing supplement should stimulate the user for an extended period of time so as to avoid an afternoon energy crash or overconsumption of stimulants.

SUMMARY OF THE INVENTION

It is an object of the present invention to provide a means to wake up on time without having to consume a stimulant immediately after awakening.

It is another object of the invention to provide a sustained supply of energizing ingredients throughout the day until a user goes to sleep at night.

It is another object of the invention to provide a temporary solution to oversleeping and fatigue.

It is another object of the invention to provide a steady supply of energizing ingredients to a user thereby suppressing the user's craving for a stimulant for an extended period of time.

It is another object of the invention to provide a time release mechanism for the energizing ingredients such that the energizing ingredients are not released immediately after ingestion.

It is another object of the invention to provide a time release mechanism for the energizing ingredients such that enough energizing ingredients are released prior to a user's awakening time thereby waking up the user at a predetermined time.

A time-release energizing supplement of the present invention comprises energizing ingredients. The energizing ingredients comprise approximately 400 mg to approximately 2200 mg of B-complex vitamins, approximately 100 mg to approximately 500 mg of guarana seed extract, approximately 8 mg to approximately 42 mg of eleuthero root extract, and approximately 100 mg to approximately 500 mg of tyrosine. The B-complex vitamins preferably comprise approximately 25 mg to approximately 125 mg of thiamin, approximately 25 mg to approximately 125 mg of riboflavin, approximately 25 mg to approximately 125 mg of niacin, approximately 25 mg to approximately 125 mg of vitamin B6, and approximately 300 mg to approximately 1700 mg of vitamin B12. Each component of the B-complex vitamins is present in at least twice the amount of Daily Reference Intakes (DRIs) set forth by National Academy of Sciences, 2004. The time-release energizing supplement further comprises an enteric coating, which controls the release of the energizing ingredients inside a user's body. The enteric coating preferably comprises ethyl cellulose, water, fractionate coconut oil, ammonium hydroxide, sodium alginate, vanillin, titanium dioxide, and stearic acid.

BRIEF DESCRIPTION OF THE DRAWINGS

A further understanding of the present invention can be obtained by reference to a preferred embodiment, along with some alternative embodiments, set forth in the illustrations of the accompanying figures. Although the illustrated embodiments are merely exemplary of systems for carrying out the present invention, the organization and method of operation of the invention in general, together with further objectives and advantages thereof, may be more easily understood by reference to the figures and the following description. The figures are not intended to limit the scope of this invention, which is set forth with particularity in the claims as appended or as subsequently amended, but merely to clarify and exemplify the invention.

For a more complete understanding of the present invention, reference is now made to the following figures.

DETAILED DESCRIPTION OF THE INVENTION

Figure 1:
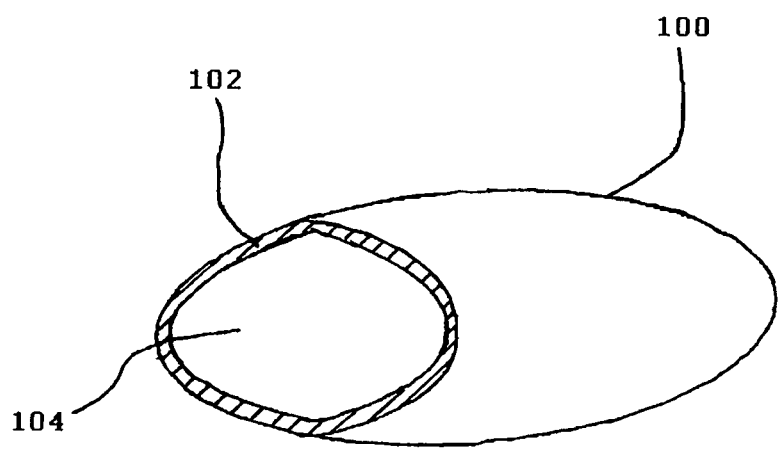
FIG. 1 is an opened view of the time-release energizing supplement, wherein the energizing ingredients and the enteric coating are depicted.

A detailed illustrative embodiment of the present invention is disclosed herein. However, the present invention may be embodied in a wide variety of forms, some of which may be quite different from those in the disclosed embodiment. Consequently, the specific ingredients and functional details disclosed herein are merely representative, yet in that regard, they are deemed to afford the best embodiment for purposes of disclosure and to provide a basis for the claims herein which define the scope of the present invention.

Moreover, well known methods and procedures for both carrying out the objectives of the present invention and illustrating the preferred embodiment are incorporated herein by reference but have not been described in detail as not to unnecessarily obscure aspects of the present invention.

The present invention relates to a time-release energizing supplement, which energizes a user by enhancing or stimulating his/her physical and mental activities. These effects may be caused directly by artificial/natural stimulants or indirectly by an ample supply of cofactors, coenzymes, enzymes, and/or precursors for neuronal or metabolic pathways. The energized state in the user also causes an overall well-being, which entails elevated mood, physical endurance, and/or increased oxygen uptake.

It is contemplated that the user will take the time-release energizing supplement of the present invention in the conventional manner with a glass of water immediately prior to going to sleep, or at least approximately 4 hours prior to the time when enhanced mental and physical activities are desired. The time-release energizing supplement can be in tablet or capsule form and can be taken daily or only at times when the user wishes to do so.

The time-release energizing supplement comprises energizing Ingredients that will physically energize the user as well as elevate his or her psychological mood. Preferred energizing ingredients and their acceptable ranges are shown in Table 1. As shown in Table 1, a preferred embodiment of the energizing ingredients comprises B-complex vitamins, eleuthero root extract, guarana seed extract, and tyrosine.

TABLE 1

A Composition of the Energizing Ingredients

| Ingredients | DRI | Range |
|---|---|---|
| Thiamin | 0.9 mg | 25-125 mg |
| Riboflavin | 0.9 mg | 25-125 mg |
| Niacin | 12 mg | 25-125 mg |
| Vitamin B6 | 1.0 mg | 25-125 mg |
| Vitamin B12 | 1.8 mg | 300-1700 mg |
| Eleuthero Root Extract | N/A | 8-42 mg |
| Guarana Seed Extract (22% Caffeine) | N/A | 100-500 mg |
| L-Tyrosine | N/A | 100-500 mg |

Preferably, the B-complex vitamins comprise thiamin, riboflavin, niacin, vitamin B-6, and vitamin B-12. A notable characteristic of this formulation is that each of the B-complex vitamins is provided in an amount quite higher than Dietary Reference Intake (DRI) values suggested by Food and Drug Administration. The DRI values are daily values for males or females between the ages of 19 and 30 years taken from "Recommended Intake for Individuals: Vitamins" National Academy of Sciences. Daily supplementation of the B-complex vitamins is generally recommended, as the B-complex vitamins cannot be stored in the body. Deficiencies of the B-complex vitamins are often associated with a decline in physical and mental performance.

Preferably, the B-complex vitamins comprise thiamin. Thiamin, also called vitamin B-1, thiamine, or aneurine hydrochloride, is a water-soluble vitamin. The most common commercial form of thiamin is thiamin mononitrate, while another less popular form of thiamin is known as Thiamine Tetrahydrofurfuryl Disulfide (TTFD). Thiamin can be rapidly converted to one of its active forms, thiamin pyrophosphate (TPP), in the brain and liver. Thiamin is essential for neural function and carbohydrate metabolism, because TPP is a coenzyme for several enzymes that are involved in cerebral glucose and energy metabolism, examples of which include pyruvate dehydrogenase, α-ketoglutarate dehydrogenase, and transketolase. Depletion of thiamin can occur as quickly as within 14 days, as there is very little thiamin stored in the body.

Preferably, the B-complex vitamins further comprise riboflavin. Riboflavin, also known as vitamin $B_2$, is an easily absorbed micronutrient and is required by all flavoproteins. As the central component of the cofactors FAD and FMN, riboflavin is required for a wide variety of cellular processes. Like the other B vitamins, it plays a key role in energy metabolism, and is required for the metabolism of fats, ketone bodies, carbohydrates, and proteins. Riboflavin is continuously excreted in the urine of healthy individuals, thus making deficiency relatively common when dietary intake is insufficient.

Preferably, the B-complex vitamins further comprise niacin. Niacin is synonymous with nicotinic acid, nicotinamide, or Vitamin B-3. It acts as a precursor to two coenzymes: nicotinamide adenine dinucleotide (NAD), which plays roles in the energy producing glycolytic pathway and citric acid cycle; and nicotinamide adenine dinucleotide phosphate (NADP), which plays roles in many anabolic reactions such as DNA repair and production of steroid hormones. Thus, Niacin can aid in constructive metabolism and energy enhancement by improving food expenditure.

Preferably, the B-complex vitamins further comprise vitamin B6. Vitamin B6 is a water-soluble vitamin which can exist in various forms, seven of which are known to date: pyridoxine, pyridoxine 5'-phosphate; pyridoxal; pyridoxal 5'-phosphate; pyridoxamine; pyridoxamine 5'-phosphate; and 4-pyridoxic acid. Pyridoxine is the form that is usually given as vitamin B6 supplement. Pyridoxal phosphate (PLP), the metabolically active form of vitamin B6, is involved in many aspects of macronutrient metabolism, neurotransmitter synthesis, histamine synthesis, hemoglobin synthesis and function and gene expression. Particularly, PLP is required for the synthesis of the neurotransmitters serotonin and melatonin, which control the circadian rhythms and modulate sleep. PLP is also required for the synthesis of norepinephrine, which as a stress hormone, gives the body sudden energy in times of stress, known as the "fight or flight" response.

Preferably, the B-complex vitamins further comprise vitamin B-12. Vitamin B-12, or cobalamine, is a water soluble vitamin with a key role in the normal functioning of the brain and nervous system, and for the formation of blood. Vitamin B-12 is the name for a class of chemically-related compounds, all of which have vitamin activity. Biosynthesis of the basic structure of the vitamin can only be accomplished by bacteria, but conversion between different forms of the vitamin can be accomplished in the human body. A common synthetic form of the vitamin, cyanocobalamin, does not occur in nature, but is used in many pharmaceuticals, supplements and as food additive, due to its stability and lower cost. In the body, vitamin B-12 is converted to the physiological forms, methylcobalamin and adenosylcobalamin. Hydroxocobalamin, methylcobalamin and adenosylcobalamin can also be found in pharmacological products and food supplements.

Vitamin B12 functions as a coenzyme for the methyl transfer reaction that converts homocysteine to methionine and also for a reaction that converts L-methyl-malonyl coenzyme A to succinyl coenzyme A. It is also required for the production of erythrocytes and neurologic function. Vitamin B12 is also considered an important supplement in the treatment of insomnia. It has been shown that administration of 3 grams a day of vitamin B12, particularly in the form of methylcobalamin, decrease sleep time yet improve sleep quality and daytime alertness in healthy men and women. (G. Mayer, *Effects of Vitamin B12 on Performance and Circadian Rhythm in Normal Subjects*, Neuropsychopharmacology, 15(5); 456-64, November (1996)).

In a preferred embodiment, the energizing ingredients comprise guarana (*Paullinia cupana*). Guarana is a shrub or small tree in the Sapindaceae family, native to Venezuela and northern Brazil. The seed of the guarana fruit is a stimulant with thermogenic and diuretic properties. The natives of the Amazonian rainforest have traditionally incorporated guarana seeds into foods and beverages to increase alertness and reduce fatigue. Studies involving guarana show benefits to acute mood and cognitive function inhuman subjects. (Haskell, et al. *A Double-Blind, Placebo-Controlled, Multi-Dose Evaluation of the Acute Behavioral Effects of Guarana in Humans*, Journal of Psychopharmacology, 21; 65-70, (2006)).

The primary active ingredients in guarana are three alkaloids called guaranine (essentially caffeine), theophylline, and theobromine. Water extracts of the guarana seed are central nervous system stimulants due to the content of these alkaloids. Guarana contains about twice the caffeine found in coffee beans (about 3-4 w/w % of caffeine in guarana seed compared to 1-2 w/w % for coffee beans). Concentrated guarana extracts, however, can contain caffeine at levels of as much as 40-50 w/w %

Guarana as a safer source of caffeine has been suggested in a study involving overweight males and guarana containing approximately 150 mg of guaranine. Surprisingly, the males showed no apparent changes in their resting heart rate or blood pressure following administration of the guarana. The same amount of caffeine as the administered guaranine would have had a marked effect on the resting heart rate of an adult male. (Sale, et al., *Metabolic and Physiological Effects of Ingesting Extracts of Bitter Orange, Green Tea and Guarana at Rest and During Treadmill Walking in Overweight Males*, International Journal of Obesity, 30; 764-773, (2006)).

Furthermore, some experts propose that the effects of guarana are more powerful and longer-lasting than caffeine alone due to additional substances in the guarana extract. For example, a 1997 study of guarana's effects on the physical activity of rats that ingested a suspension of guarana showed increased memory retention and physical endurance compared to rats that ingested a solution of caffeine alone. (Espinola E B, et al., *Pharmacological Activity of Guarana (Paullina cupana Mart.) in Laboratory Animals*, Journal of Ethnopharmacology, 55(3); 223-9, (1997)). Other studies have demonstrated additional benefits of guarana such as antioxidant, antibacterial, and fat cell reducing properties.

Preferably, the energizing ingredients further comprise tyrosine. Tyrosine (abbreviated as Tyr or Y) or 4-hydroxyphenylalanine, is one of the 20 amino acids. Since L-amino acids represent the vast majority of amino acids found in proteins, L-tyrosine is preferred in the present invention and will be synonymous with "Tyrosine" throughout this disclosure.

Tyrosine is a starting material for neurotransmitters and increases plasma neurotransmitter levels (particularly dopamine and norepinephrine). Based on this fact, tyrosine has been proposed as a treatment for various conditions in which mental function is impaired or slowed down, such as fatigue and depression.

Tyrosine has been evaluated in a number of animal and human studies for its usefulness as a nutritional supplement. Tyrosine appears to prevent the substantial decline in various aspects of cognitive performance and mood associated with a variety of acute stress, such as stress, cold, fatigue, and sleep deprivation. (H. Lieberman, *Nutrition, Brain Function and Cognitive Performance*, Appetite, 40; 245-254, (2003)). In fact, the Committee on Military Nutrition Research concluded that tyrosine was a leading candidate as a cognitive performance enhancer in military operations (Same).

A daily dosage generally recommended by World Health Organization is about 25 mg/kg body weight for an adult. The usual dosage amounts to 500-1500 mg per day. It is not recommended to exceed 12 g per day. In fact, too high doses result in reduced levels of dopamine.

Preferably, the energizing ingredients of the present invention further comprise eleuthero root extract. Eleuthero root is obtained from the plant *Eleutherococcus senticosus*, commonly called eleuthero. Eleuthero is a thorny shrub native to East Russia, Northeast China, Korea, and Japan. Typically, the root of eleuthero is used medicinally. Eleuthero is also known as eleuthero ginseng or Siberian ginseng.

Eleuthero's active ingredients are a group of compounds called eleutherosides. To date, seven primary eleutherosides have been identified, with most of the research attention focusing on eleutherosides B and E. Eleuthero is an "adaptogen," an agent that helps the body adapt to stress. It is thought to help support adrenal gland function when the body is challenged by stress. (Gaffney, et al., *Panax Ginseng and Eleutherococcus Senticosus May Exaggerate an Already Existing Biphasic Response to Stress via Inhibition of Enzymes which Limit the Binding of Stress Hormones to Their Receptors*, Medical Hypothesis, 56; 567-572, (2001)).

Eleuthero is believed to enhance mental acuity and physical endurance without the energy crash that comes with caffeinated products. Moreover, research has shown that eleuthero improves the use of oxygen by the exercising muscle. (K. Asano, et al., Effect of *Eleutherococcus Senticosus* Extract on Human Working Capacity. Planta Medica, 37; 175-177, (1986)). This means that a person is able to maintain aerobic exercise longer and recover from the workout more quickly. In addition, eleuthero herb is widely used as anticholesteremic, mildly anti-inflammatory agent and antioxidant.

Dried, powdered root and rhizomes of eleuthero are commonly used in an approximate dosage of 2-3 grams per day. Alternatively, 300-400 mg per day of concentrated solid extract standardized on eleutherosides B and E can be used, as can alcohol-based extracts. Eleuthero can be combined with other adaptogens, like Korean ginseng, Panax ginseng, astragalus, or schisandra, to increase its effectiveness. It is contemplated that Panax Ginseng may partially or wholly substitute Eleuthero Root Extract.

The energizing ingredients may further comprise vitamins such as Vitamin A, C, and/or E. Vitamins A, C, and E, in addition to their regulatory effects on the body's biochemical activities, provide antioxidative benefits. Such antioxidative properties of vitamins A, C, and E are thought to scavenge free radicals that are generated by heightened biochemical activities of the energized user.

The energizing ingredients may further comprise minerals such as calcium, magnesium, iron, or selenium. In particular, selenium is thought to provide diverse benefits to the user's body. As a constituent of selenoproteins, selenium, an essential trace mineral, has structural and enzymatic roles, in the latter context being best-known as an antioxidant and catalyst for the production of active thyroid hormone. Selenium is needed for the proper functioning of the immune system and deficiency of which has been linked to adverse mood states. (M. P. Rayman, *The Importance of Selenium to Human Health*, The Lancet, 356(9225); 233-41, (2000)).

The energizing ingredients of the time-release energizing supplement are released gradually inside the user's body, preferably in the small intestine, by a means of delayed release mechanism.

The mechanism of delayed release allows the energizing ingredients to steadily energize the user for approximately 8 hours after the user begins to feel the effects of the energizing ingredients. Generally, the user starts to feel energized approximately 4 hours after the ingestion of the time-release energizing composition. The user does not experience the energy crash typical for coffee, energy drinks, or energy supplements due to the controlled and sustained release of the energizing ingredients. The time-release energizing supplement of the present invention can be taken daily or only at times when the user wishes to do so.

If the time-release energizing supplement is taken at a predetermined time prior to falling asleep at night, the energizing ingredients will be slowly released into the user's blood stream during the course of the night. The user will then wake up in the morning, feeling alert and full of energy due to the release of the ingredients while asleep. This method significantly increases the likelihood of the user waking up on time, compared to a method wherein a stimulant is consumed in the morning.

The stimulating effects of the energizing ingredients of the present invention last for several hours after awakening, as the release of the ingredients is gradual and controlled. The stimulating effect typically lasts for up to about 8 hours after the user begins to feel energized, though this varies among individuals.

The sustained, delayed release mechanism of the energizing ingredients in the present invention has several advantages over immediately-release methods. First, it allows the user to take the energizing ingredients in advance thereby obviating the inconvenience to consume a stimulant in the morning or anytime after the user first becomes aware of the "energy crash". Secondly, by providing a steady supply of energizing ingredients, the present invention prevents the user's need to consume additional energy-boosting agents such as caffeine. It has been reported that insomnia may be linked to the total amount of caffeine consumed during the day rather than the time at which caffeine is taken before retiring. (A. Nehlig, et al., *Caffeine and the Central Nervous System: Mechanisms of Action, Biochemical, Metabolic and Psychostimulant Effects*, Brain Research, 17; 139-170, (1992)). Therefore, the delayed mechanism of the present invention indirectly prevents insomnia and other symptoms caused by excessive caffeine intake by limiting the total amount of caffeine consumed during the day.

The delayed release mechanism preferably utilizes an enteric coating. The enteric coating is a barrier applied to oral medication or supplement and prevents release of the content before it reaches the small intestine. Substances comprising an enteric coating are relatively stable in the highly acidic environment of the stomach and dissolves relatively easily in the less acidic environment of the small intestine. Preferably, the enteric coating limits the release of the energizing ingredients to approximately 55% by the 4th hour of ingestion. The rate of release is controlled by the degradation of the coating and/or by the diffusion of the energizing ingredients.

Some examples of substances that may be used to make the enteric coatings are, but not limited to, ethyl cellulose, cellulose acetate phthalate (CAP), methyl acrylate-methacrylate acid copolymers, cellulose acetate succinate, hydroxy propyl methyl cellulose phthalate, hydroxy propyl methyl cellulose acetate succinate (hypromellose acetate succinate), polyvinyl acetate phthalate (PVAP), and methyl methacrylate-methacrylic acid copolymers, and mixtures thereof.

Preferably, the enteric coating comprises ethyl cellulose, water, fractionate coconut oil, ammonium hydroxide, sodium alginate, vanillin, titanium dioxide, and stearic acid.

The following examples further describe and demonstrate embodiments within the scope of the invention. The examples are given solely for the purpose of illustration and are not to be construed as limitations of the present invention, as many variations are possible without departing from the spirit and scope of the invention.

EXAMPLE 1

| Ingredients | Amount | DRI | % w/w |
|---|---|---|---|
| Thiamin mononitrate | 75 mg | 0.9 mg | 3.90% |
| Riboflavin | 75 mg | 0.9 mg | 3.90% |
| Niacin amide | 75 mg | 12 mg | 3.90% |
| Pyridoxine HCl | 75 mg | 1.0 mg | 3.90% |
| Cyanocobalamin | 1000 mg | 1.8 mg | 51.95% |
| Eleuthero Root Extract | 25 mg | N/A | 1.30% |
| Guarana Seed Extract (22% caffeine) | 300 mg | N/A | 15.6% |
| L-Tyrosine | 300 mg | N/A | 15.6% |

EXAMPLE 2

| Ingredients | Amount | DRI | % w/w |
|---|---|---|---|
| Thiamin mononitrate | 75 mg | 0.9 mg | 1.01% |
| Riboflavin | 75 mg | 0.9 mg | 1.01% |
| Niacin amide | 75 mg | 12 mg | 1.01% |
| Pyridoxine HCl | 75 mg | 1.0 mg | 1.01% |
| Cyanocobalamin | 1000 mg | 1.8 mg | 13.5% |
| Eleuthero Root Extract | 25 mg | N/A | 0.34% |
| Guarana Seed Extract (22% caffeine) | 300 mg | N/A | 4.04% |
| L-Tyrosine | 300 mg | N/A | 4.04% |
| Vitamin A | 5000 mg | 0.7-0.9 mg | 67.3% |
| Vitamin C | 300 mg | 75-90 mg | 4.04% |
| Vitamin E | 200 mg | 15 mg | 2.69% |
| Selenium | 200 mcg | 45 mcg | 0.0027% |

The energizing ingredients as shown in Examples 1 and 2 are intended to be released via the delayed release mechanism. This means that the energizing ingredients are released at a time later than that immediately following its administration. Most preferably, this is achieved by encapsulating the compositions of Examples 1 and 2 with the enteric coating comprising ethyl cellulose, water, fractionate coconut oil, ammonium hydroxide, sodium alginate, vanillin, titanium dioxide, and stearic acid.

FIG. 1 is an opened view of an exemplary embodiment of the present invention. A tablet 100 comprises the energizing ingredients 104 as discussed above, and an enteric coating 102 surrounding the energizing ingredients so as to control the release of the energizing ingredients after the tablet 100 is ingested by a user.

Figure 2:
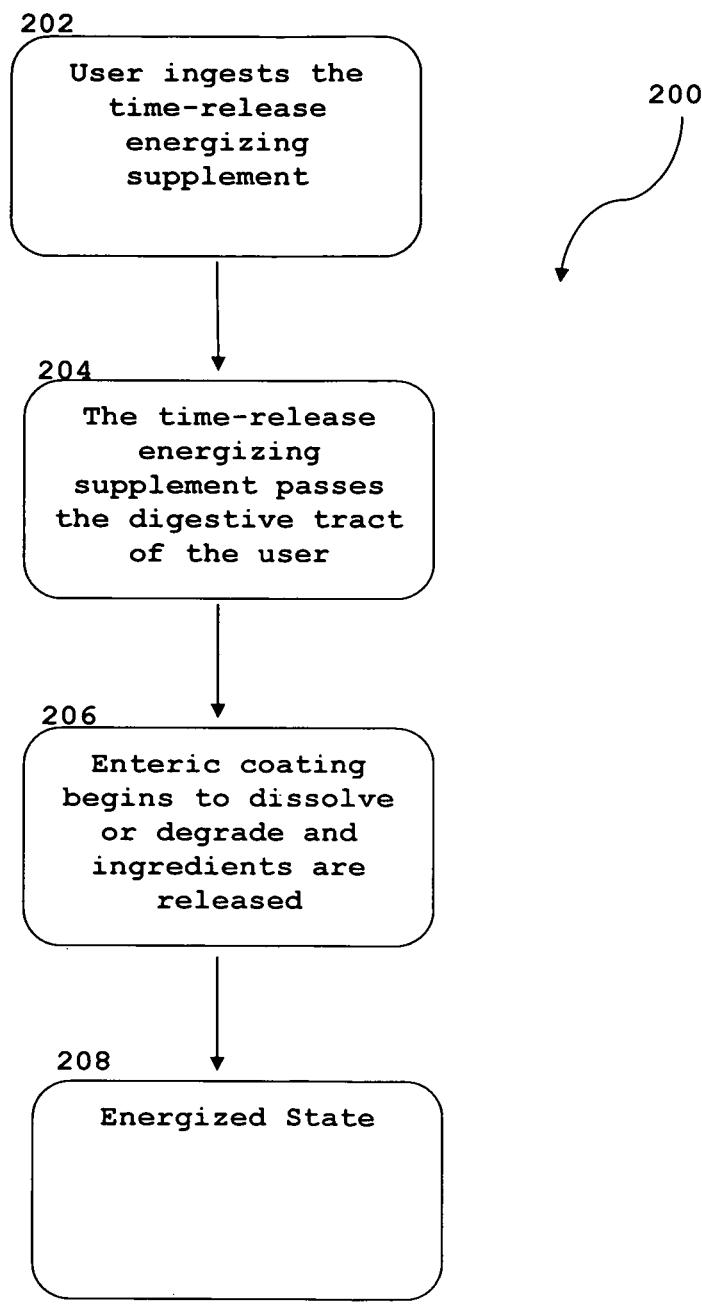
FIG. 2 is a flow chart illustrating chronological steps by which the energizing tablet energizes the user.

FIG. 2 describes exemplary steps whereby the user of the time-release energizing supplement is energized. The process begins with step 202 wherein the user ingests the energizing ingredients that are coated with the enteric coating (i.e., the time-release energizing supplement). Step 204 and 206 comprise a waiting period during which the user does not feel the effects of the energizing ingredients. The waiting period should be approximately 4 to approximately 8 hours on average, although this varies depending on the user's physiological parameters such as his/her rate of metabolism, height, weight, etc. In step 206, the enteric coating begins to dissolve or degrade in the user's small intestine and the ingredients begin to be released. The user will then be in an energized state 208 which begins sometime after the initial release of the ingredients into the user's system. Typically, the energizing state 208 lasts for about up to 8 hours after the user begins to feel energized. However, as with the waiting period, the duration of the energizing effects also varies depending on the user.

DISSOLUTION STUDY

A dissolution study was conducted on the time-release energizing supplement in the form of a tablet. A total of 6 tablets containing the identical ingredients were tested one at a time. Each tablet contained, on average, approximately 33 mg of caffeine. The enteric coating of the tablet used in the study comprised ethyl cellulose, fractionate coconut oil, ammonium hydroxide, sodium alginate, vanillin, titanium dioxide, and stearic acid. Each tablet was immersed in 1000 mL of 0.1N HCl solution (HCl Solution) while stirring. The amount of caffeine dissolved in the solution was measured at $4^{th}$, $6^{th}$, and $8^{th}$ hours after the initial immersion of the tablet. Time 0 is the time at which the tablet came in contact with the HCl Solution. The HCl Solution containing the tablet was continuously stirred over the 8 hour period. The amount of caffeine released into the solution was measured with HPLC. Average values of dissolved caffeine for the 6 tablets at each time point were calculated and summarized in Table 2.

TABLE 2

| Time (Hours) | Amount of Caffeine dissolved in the solution (mg/tablet) | % caffeine dissolved in the solution (w/w %) |
| --- | --- | --- |
| 4.00 | 18.197 | 55.14 |
| 6.00 | 27.069 | 82.03 |
| 8.00 | 32.912 | 99.73 |

Figure 3:
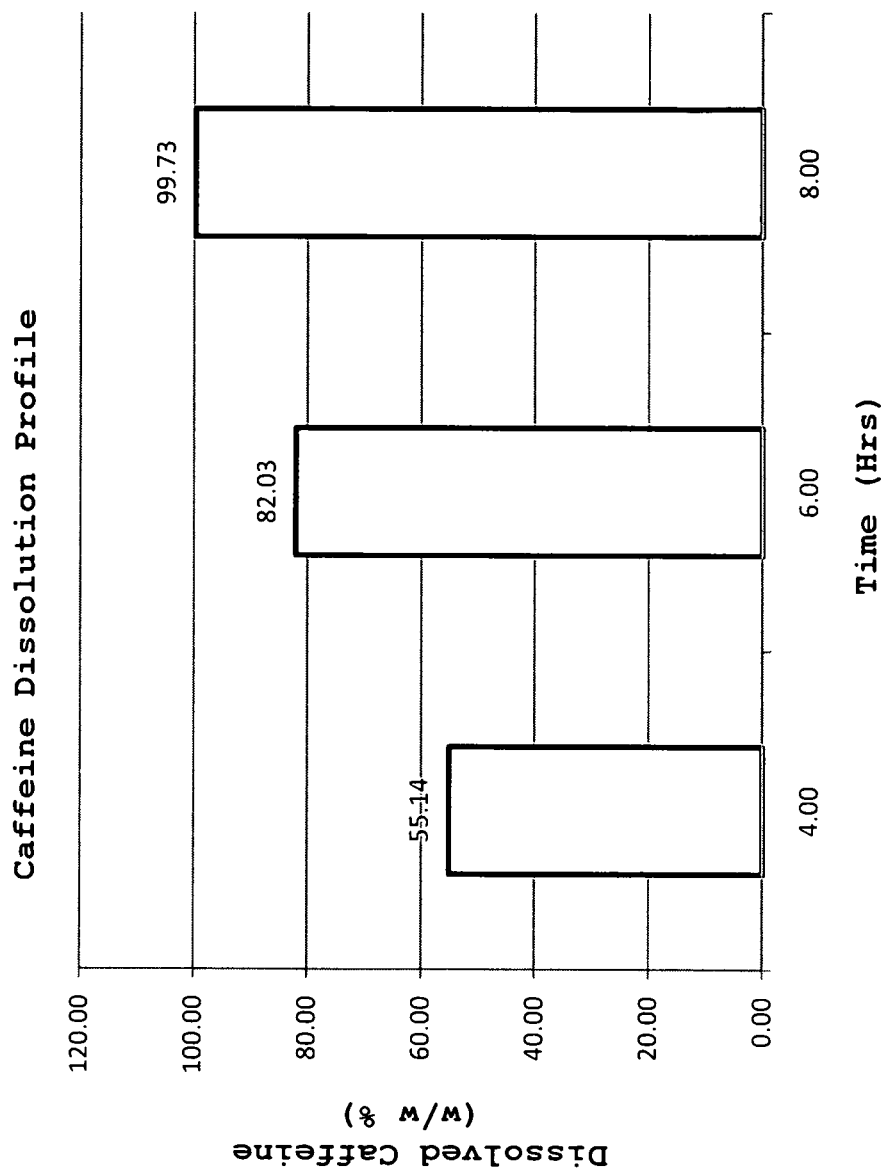
FIG. 3 is a chart showing the results of a dissolution study conducted on a preferred embodiment of the time-release energizing supplement.

FIG. 3 shows a chart of the dissolution study results. The horizontal axis represents time in hours and the vertical axis represents w/w % caffeine dissolved in the solution relative to the initial amount of caffeine in the tablet. Time 0 represents the time at which the tablet comes in contact with the stomach acid (i.e., the HCl Solution). As evident from FIG. 3, the enteric coating of the present invention releases more than half of its caffeine content by about 4 hours following the submersion of the tablet in the solution. By the $8^{th}$ hour, caffeine is almost completely released.

While the present invention has been described with reference to the preferred embodiment and alternative embodiments, which have been set forth in considerable detail for the purposes of making a complete disclosure of the invention, such embodiments are merely exemplary and are not intended to be limiting or represent an exhaustive enumeration of all aspects of the invention. The scope of the invention, therefore, shall be defined solely by the following claims. Further, it will be apparent to those of skill in the art that numerous changes may be made in such details without departing from the spirit and the principles of the invention. It should be appreciated that the present invention is capable of being embodied in other forms without departing from its essential characteristics.

What is claimed is:

1. A method of enhancing energy in a user with a delayed mechanism:
    a) providing a time-release energizing supplement comprising energizing ingredients including approximately 25 mg to approximately 125 mg of thiamin, approximately 25 mg to approximately 125 mg of riboflavin, approximately 25 mg to approximately 125 mg of niacin, approximately 25 mg to approximately 125 mg of vitamin B6, approximately 300 mg to approximately 1700 mg of vitamin B12, approximately 100 mg to approximately 500 mg of guarana, approximately 8 mg to approximately 42 mg of ginseng extract, and approximately 100 mg to approximately 500 mg of L-Tyrosine;
    b) orally administering said time-release energizing supplement to said user at a first predetermined time prior to falling asleep; and
    c) releasing said energizing ingredients from said time-release energizing supplement following said administration of said time-release energizing supplement to facilitate awakening of said user from sleep at a second predetermined time, wherein said second predetermined time is later than said first predetermined time.

2. The method of claim 1 wherein said time-release energizing supplement is a tablet with an enteric coating.

3. A time-release energizing supplement according to claim 1, wherein said ginseng is selected from the group consisting of eleuthero and Panax Ginseng.

4. The method of claim 1 wherein said thiamin is present in an approximate amount of 75 mg.

5. The method of claim 1 wherein said riboflavin is present in an approximate amount of 75 mg of riboflavin.

6. The method of claim 1 wherein said niacin is present in an approximate amount of 75 mg.

7. The method of claim 1 wherein said vitamin B6 is present in an approximate amount of 75 mg.

8. The method of claim 1 wherein said ginseng extract is present in an approximate amount of 25 mg.

9. The method of claim 1 wherein said guarana is present in an approximate amount of 300 mg.

10. The method of claim 1 wherein said L-Tyrosine is present in an approximate amount of 300 mg.

11. The method of claim 1 wherein said energizing ingredients are substantially free of carnitine, lipoic acid, and creatine.

12. The method of claim 1 wherein said vitamin B12 is present in an approximate amount of 1000 mg.

13. The method of claim 1 wherein said guarana contains at least 22 w/w % of a stimulant.

14. The method of claim 1 wherein the energizing ingredients comprising: 75 mg thiamin; 75 mg riboflavin; 75 mg niacin; 75 mg vitamin B6; 1000 mg vitamin B12; 300 mg guarana; 25 mg of ginseng extract ; and 300 mg L-Tyrosine.

15. The method of claim 1, wherein the energizing ingredients further comprising at least one selected from the group consisting of: approximately 5000 mg of vitamin A, approximately 300 mg of vitamin C, and approximately 200 mg of vitamin E.

16. The method of claim 1, wherein the energizing ingredients further comprising at least one selected from the group consisting of: calcium, magnesium, iron, and selenium.

17. A method of facilitating awakening of a user from sleep comprising:
   a) providing a time-release energizing supplement comprising energizing ingredients including approximately 100 mg to approximately 500 mg of guarana, approximately 8 mg to approximately 42 mg of ginseng extract, approximately 100 mg to approximately 500 mg of L-Tyrosine, and B-complex vitamins comprising approximately 25 mg to approximately 125 mg of thiamin, approximately 25 mg to approximately 125 mg of riboflavin, approximately 25 mg to approximately 125 mg of niacin, approximately 25 mg to approximately 125 mg of vitamin B6, and approximately 300 mg to approximately 1700 mg of vitamin B12;
   b) orally administering said time-release energizing supplement to said user at a first predetermined time prior to falling asleep;
   c) releasing said energizing ingredients from said time-release energizing supplement following said administration of said time-release energizing supplement; and
   d) facilitating awakening of said user from sleep at a second predetermined time through said release of said energizing ingredients.

18. The method of claim 2 wherein said enteric coating comprises ethyl cellulose, water, fractionate coconut oil, ammonium hydroxide, sodium alginate, vanillin, titanium dioxide, and stearic acid.

19. The method of claim 2 wherein the enteric coating limits the release of the energizing ingredients to approximately 55% by fourth hour of ingestion.

20. A method of facilitating awakening of a user from sleep comprising:
   a) providing a time-release energizing supplement comprising energizing ingredients consisting essentially of approximately 100 mg to approximately 500 mg of guarana, approximately 8 mg to approximately 42 mg of ginseng extract, approximately 100 mg to approximately 500 mg of L-Tyrosine, and B-complex vitamins comprising approximately 25 mg to approximately 125 mg of thiamin, approximately 25 mg to approximately 125 mg of riboflavin, approximately 25 mg to approximately 125 mg of niacin, approximately 25 mg to approximately 125 mg of vitamin B6, and approximately 300 mg to approximately 1700 mg of vitamin B12;
   b) orally administering said time-release energizing supplement to said user at a first predetermined time prior to falling asleep;
   c) releasing said energizing ingredients from said time-release energizing supplement following said administration of said time-release energizing supplement; and
   d) facilitating awakening of said user from sleep at a second predetermined time through said release of said energizing ingredients.

\* \* \* \* \*